(12) United States Patent
Bae

(10) Patent No.: US 6,552,316 B1
(45) Date of Patent: Apr. 22, 2003

(54) GLARE PROTECTING DEVICE UTILIZING BOTH OPTICAL AND NON-OPTICAL DETECTORS AND METHOD OF CONTROLLING THEREOF

(75) Inventor: Young Dawn Bae, Suwon (KR)

(73) Assignee: Otos Co., Ltd. (KR)

( * ) Notice: Subject to any disclaimer, the term of this patent is extended or adjusted under 35 U.S.C. 154(b) by 0 days.

(21) Appl. No.: 09/465,894

(22) Filed: Dec. 17, 1999

(30) Foreign Application Priority Data

Dec. 29, 1998 (KR) .............................. 98-60014
Dec. 29, 1998 (KR) .............................. 98-60015

(51) Int. Cl.$^7$ .................................................. G01J 1/20
(52) U.S. Cl. ...................................... 250/201.1; 349/14
(58) Field of Search .......................... 250/201.1, 208.2, 250/214 R, 214 AL, 206; 349/13, 14, 116, 172; 2/8

(56) References Cited

U.S. PATENT DOCUMENTS

| | | | |
|---|---|---|---|
| 5,444,232 A | * | 8/1995 | Gunz et al. .............. 250/201.1 |
| 5,751,258 A | | 5/1998 | Fergason et al. |
| 5,793,449 A | | 8/1998 | Lagerwall |
| 5,825,441 A | | 10/1998 | Hornell et al. |
| 5,857,215 A | | 1/1999 | Fergason et al. |
| 5,880,793 A | | 3/1999 | Gunz et al. |
| 5,930,047 A | | 7/1999 | Gunz et al. |
| 5,959,705 A | | 9/1999 | Fergason |

* cited by examiner

Primary Examiner—Stephone B. Allen
Assistant Examiner—Bradford Hill
(74) Attorney, Agent, or Firm—Cantor Colburn LLP

(57) ABSTRACT

A glare protecting device for protecting a worker's eyes from a light comprising a solar cell for generating a solar voltage when the light is applied thereto; an optical detector for generating a light detecting signal by detecting the light; a non-optical detector for generating an electromagnetic wave detecting signal by detecting an electromagnetic wave; a controller transferring to an operating mode when the light detecting signal is changed, disabling a driving control signal when the driving control signal is enabled, generating a starting signal and enabling the driving control signal in case that the light and/or electromagnetic wave detecting signal is produced when the driving control signal is disabled, and then transferring to a stop mode; a driving means for generating a driving signal by inputting a starting voltage in response to the starting signal and a driving voltage in response to the driving signal; and a glare protecting plate which is driven in response to the driving signal.

16 Claims, 4 Drawing Sheets

GLARE PROTECTING DEVICE UTILIZING BOTH OPTICAL AND NON-OPTICAL DETECTORS AND METHOD OF CONTROLLING THEREOF

BACKGROUND OF THE INVENTION

1. Field of the Invention

The present invention relates to a glare protecting device and a method of controlling thereof, more particularly, for automatically controlling the transmission of light generated by a welding or cutting torch.

2. Description of the Prior Art

A glare protecting device is used to protect a worker's eyes from light generated by a welding or cutting torch. With this glare protecting device, radiation above 780 nm(IR) and below 365 nm(UV) are filtered, and only the radiation in the visible range is dimmed.

U.S. Pat. No. 5,315,099 discloses a glare protecting device comprising a glare protecting plate, an electronic circuit connected to the glare protecting plate for applying an electric operating voltage thereto, and a light sensor which detects a light and applies a signal corresponding to the detected signal to the electronic circuit.

U.S. Pat. No. 5,444,232 discloses a glare protecting device comprising a glare protecting plate, an optical signal detector for producing a dimming signal, an evaluating circuit for controlling the glare protecting plate, and a controller for controlling the brightening time of the glare protecting plate and detecting the intensity of the light impinging on the light sensor. The controller is connected to a timing generator to detect the duration of the dimming signal produced by the detector, and comprises means to interlink the acquired data with respect to logic and/or time.

The device disclosed in U.S. Pat. No. 5,444,232 detects the light intensity or the amount of light, and the welding duration, and interconnects these parameters with respect to logic and/or time by means of a suitable controller, thereby optimizing the brightening time.

The configuration of this device is simple, but time is delayed from an input of the welding light to an operation of a glare protecting device, and the power consumption is increased to operate a controller including a microcomputer for detecting a consistent change of the input light.

Products having an automatic off function for preventing continuous current consumption should manipulate an on-switch to restart, and should control the sensitivity of input light according to the condition of the welding.

Also, in an arrangement involving detecting the welding state by using a photo signal, a conventional glare protecting device can malfunction since a different signal would be detected depending on the welding and the kind of a welding machine.

Therefore, a glare protecting device using a non-optical detector composed of a transformer has been developed. But, when a magnetic field caused by surrounding noise impacts this device, the noise magnetic field continuously causes an unintentional malfunction and generates the light shutting phenomenon in the glare protecting plate, so that a worker cannot perceive the welding light with his eyes and cannot check the welding state.

SUMMARY OF THE INVENTION

An object of the present invention is to provide a glare protecting device with reduced power consumption.

Another object of the present invention is to provide a glare protecting device which can prevent malfunction and protect a worker's eyes safely by detecting light, electromagnetic waves, and temperature.

Still another object of the present invention is to provide a method of controlling a glare protecting device to accomplish the above objects.

To accomplish the above objects, pursuant to the present invention, a glare protecting device for protecting eyes from a light is provided which comprises:

a solar cell which generates a solar voltage when the light is applied thereto;

an optical detector for generating a light detecting signal by detecting the light;

a non-optical detector for generating an electromagnetic wave detecting signal by detecting an electromagnetic wave;

a controller shifting to an operating mode when the light detecting signal is changed, disabling a driving control signal when the driving control signal is enabled, generating a starting signal and enabling the driving control signal in the event that the light and/or electromagnetic wave detecting signal is produced when the driving control signal is disabled, and then shifting to a stop mode;

a driving means for generating a driving signal by inputting a starting voltage in response to the starting signal and a driving voltage in response to the driving signal; and a glare protecting plate which is driven in response to the driving signal;

to accomplish still another of the above object, pursuant to the present invention, a method of controlling a glare protecting device is provided comprising:

a light detector which detects a light and generates a light detecting signal;

an electromagnetic wave detector which detects an electromagnetic wave and generates an electromagnetic detecting signal;

a glare protecting plate for protecting eyes from the light; and a controller which inputs the light and the electromagnetic wave for controlling on/off of the glare protecting plate, wherein the method comprises steps of:

shifting to an operating mode when the light detecting signal is changed;

operating the glare protecting plate to be turned on in the event that the glare protecting plate is turned off in the operating mode and the light and/or electromagnetic wave detecting signals are generated, and to be turned off in the event that the glare protecting plate is turned on; and shifting to a stop mode after the operating step of the glare protecting plate.

Further objects and advantage of the invention can be more fully understood from the following detailed description taken in conjunction with the accompanying drawings.

DETAILED DESCRIPTION OF THE INVENTION

Figure 1:
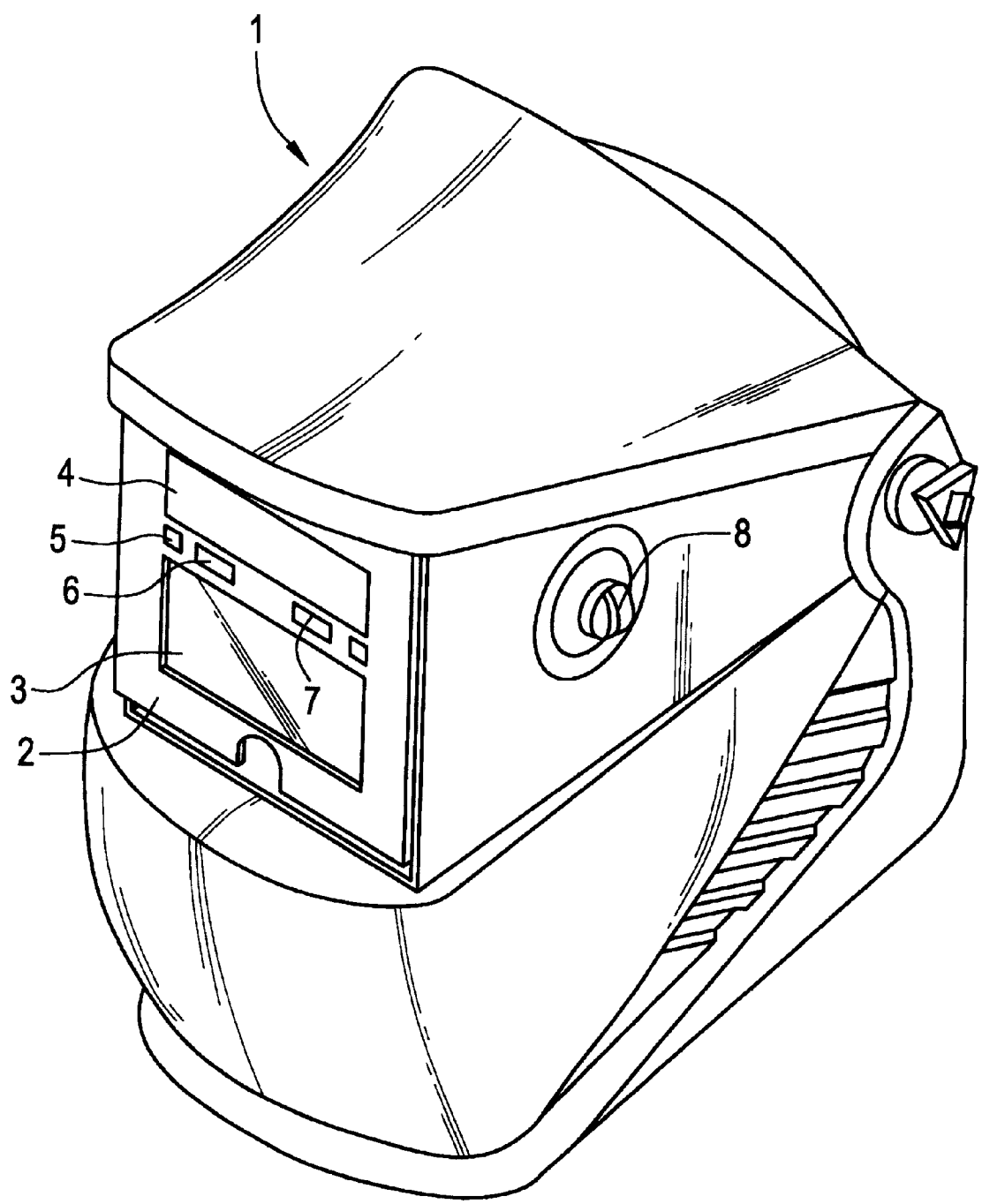
FIG. 1 illustrates a protective mask having a glare protecting device.

FIG. 1 illustrates a protective mask having a glare protecting device. The protective mask 1 comprises, a glare protecting device 2, a glare protecting plate 3, a solar cell 4, a light sensor 5, a temperature sensor 6, an antenna 7, and an intensity control switch 8.

As shown in FIG. 1, the glare protecting device 2 is disposed at the front side of the protective mask 1. The glare protecting device 2 has a controller(not shown) to regulate a glare protecting plate 3 to protect a worker's eyes from a high intense light. The glare protecting plate 3 is transparent when a light is not applied, thereto, but it is dimmed when a light impinges thereon. The solar cell 4 generates a voltage in the event that light is applied thereto. The light sensor 5 detects a light in the event that the light is applied thereto. The temperature sensor 6 detects the surrounding temperature. The antenna 7 receives the surrounding electromagnetic waves. The intensity control switch 8 is composed of a volume switch and controls the intensity of the glare protecting plate 3.

Accordingly, the glare protecting device 2 shown in FIG. 1 detects the surrounding light and electromagnetic waves by means of the light sensor 5 and the antenna 7. Then, the controller(not shown) receives input from the light sensors and the antenna 7 and controls operation of glare protecting plate 3 which is dimmed in order to protect eyes of a worker wearing the protective mask 1. Also, in the event that temperature detected by the temperature sensor 6 is low, the controller(not shown) accelerates the response time of the glare protecting plate 3.

Figure 2:
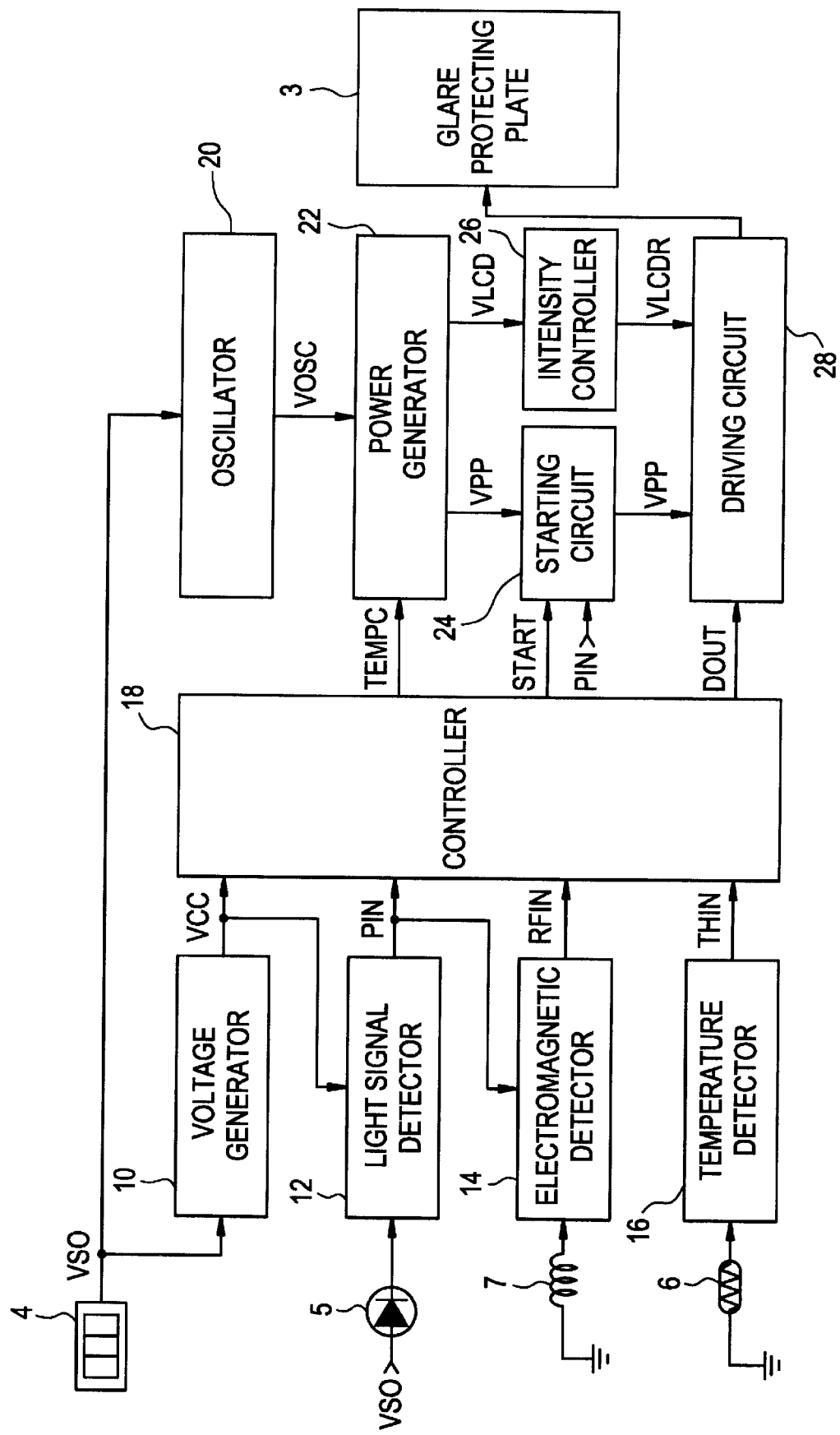
FIG. 2 is a block diagram of a glare protecting device according to the present invention.

FIG. 2 is a block diagram of a glare protecting device, comprising a voltage generator 10, a light signal detector 12, an electromagnetic wave detector 14, a temperature detector 16, a controller 18, an oscillator 20, a power generator 22, a starting circuit 24, an intensity controller 26, and a driving circuit 28.

Referring to FIG. 2, a solar cell 4, a light sensor 5, an antenna 7, a temperature sensor 6, and a glare protecting plate 3 have the identical numerals with those of FIG. 1. In a preferred embodiment, the light sensor 5 can be a photodiode, the antenna 7 can be a coil, and the temperature sensor 6 can be a thermistor.

Functions of blocks illustrated in FIG. 2 are described as below.

The solar cell 4 generates a voltage VSO when a light is applied thereto. The voltage generator 10 inputs the voltage VSO and generates a voltage VCC. The voltage generator 10 is a charging circuit including a lithium cell(not shown) as a charging battery, and outputs the charged voltage VCC to the controller 18.

When voltage VSO is generated, the light signal detector 12 detects the surrounding light by means of the light sensor 5 and generates a light detecting signal PIN. The light signal detector 12 generates the light detecting signal PIN when a light emitted by the welding or the cutting torch is detected by the light sensor 5. It is preferred that the light signal detector 12 comprises a filter and an amplifier for detecting only a light signals of an effective band.

Accordingly, the solar cell 4 and the light signal detector 12 are optical detectors for detecting the surrounding light.

The electromagnetic wave detector 14 detects a frequency signal of an effective band and generates an electromagnetic wave detecting signal RFIN when an electromagnetic wave is inputted through the antenna 7. It is preferred that the electromagnetic wave detector 14 comprises a resonator, a filter and a comparator for receiving a specific frequency band from an electromagnetic wave received from the antenna 7. Accordingly, when the electromagnetic wave detector 14 detects an electromagnetic wave generated in the welding and the cutting torch, it generates the electromagnetic wave detecting signal RFIN.

The temperature detector 16 generates a temperature detecting signal THIN corresponding to the surrounding temperature that is detected by a thermistor 6.

Accordingly, the electromagnetic wave detector 14 and the temperature detector 16 are non-optical detectors which detect the surroundings frequency and temperature.

The controller 18 inputs and processes the light detecting signal PIN, the electromagnetic wave detecting signal RFIN, and the temperature detecting signal THIN outputted from the light signal detector 12, the electromagnetic wave detector 14 and the temperature detector 16, and generates a starting signal START for controlling the starting circuit 24 and a driving control signal DOUT for controlling the driving circuit 28. It is preferred that the controller is a microcomputer.

The oscillator 20 inputs the voltage VSO and generates an oscillating voltage VSO. The oscillating voltage is a signal of a pulse type.

The power generator 22 inputs and boosts the oscillating voltage VSO, and generates a starting voltage VPP and a driving voltage VLCD. It is preferred that the power generator 22 includes a voltage doubler rectifier circuit composed of a capacitor.

The starting circuit 24 outputs the starting voltage VPP in response to the starting signal START or the light detecting signal PIN.

The intensity controller 26 controls the driving voltage VLCDR by controlling the driving voltage VLCD by means of the intensity control switch 8.

The driving circuit 28 selects a voltage outputted from the starting circuit 24 in response to the starting signal START or the light detecting signal PIN at the time of starting. And at the time of driving, the driving circuit 28 selects the driving voltage VLCDR in response to the driving control signal DOUT and generates a driving signal for driving the glare protecting plate 3. At this time, the driving signal is a square-wave signal.

In an embodiment wherein the glare protecting plate 3 is composed of a liquid crystal display device, the driving circuit 28 selects the driving voltage VLCDR in response to the driving control signal DOUT, and selects the starting voltage VPP in response to the starting signal START or the light detecting signal PIN to generate a driving signal.

Accordingly, the driving circuit 28 selects and outputs a high starting voltage VPP at the time of starting of the glare protecting plate 3. After starting the glare protecting plate 3, the driving circuit 28 selects and outputs the driving voltage VLCDR lower than the starting voltage VPP.

Figure 3:
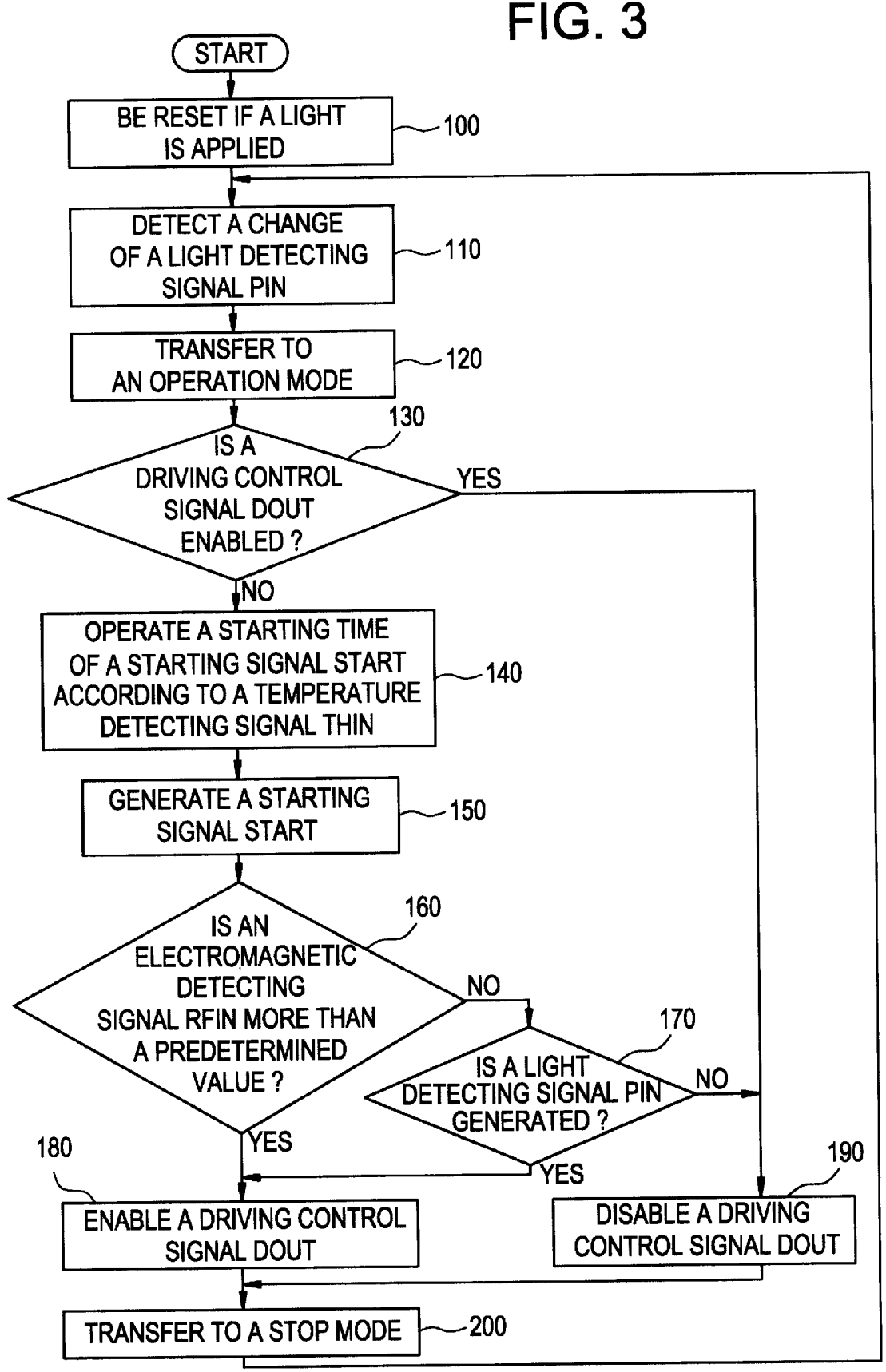
FIG. 3 is a flow chart depicting an operation of a controller of the glare protecting device of FIG. 2.

FIG. 3 is a flow chart showing operation of a controller for the glare protecting device according to the present invention. The operation of the glare protecting device of the present invention is described as below referring to FIG. 3.

The solar cell 4 generates a voltage VSO in the event that a light is applied thereto, and a voltage generator 10 produces a voltage VCC. The controller 18 is reset for processing a signal to be inputted when the voltage VCC is applied thereto(Step 100).

The light sensor 5 is turned on in the event that the voltage VSO is generated. The light signal detector 12 detects a light signal of an effective frequency band in signals applied from the light sensor 5, and generates the light detecting signal PIN. The controller 18 detects a change of the light detecting signal PIN(Step 110).

Accordingly, when the light detecting signal PIN stored in an internal resistor(not shown) of the controller 18 is "1" when the controller 18 is reset by applying a power supply thereto, and the light detecting signal PIN is "0" when the light signal detector 12 detects a light signal, the controller 18 detects that the light detecting signal PIN changes to "0". Of course, a reverse change can be detected. Accordingly, the controller 18 detects two cases: that the surrounding light disappears, and that the surrounding light appears.

The controller 18 is shifted to an operating mode in case that the light detecting signal PIN is changed(Step 120).

The controller 18 determines whether the driving control signal DOUT is in a enable state or not(Step 130).

As a result of the determination of Step 130, in the event that the driving control signal DOUT is in an enable state, the driving control signal DOUT is disabled at Step 190.

As a result of the determination of Step 130, in the event that the driving control signal DOUT is not in an enable state, the controller 18 regulates the starting time of the starting signal START according to the temperature detecting signal THIN inputted from the temperature detector 16(Step 140). That is, in the event that the temperature detecting signal THIN appears to indicate a low temperature, the controller 28 performs an operation for compensating a temperature and regulates the starting time of the starting signal START. Accordingly, the glare protecting plate can be rapidly operated even in low temperatures.

The controller 18 outputs the starting signal START to the starting circuit 24(Step 150). The starting circuit 24 generates the voltage VPP in response to the light detecting signal PIN of the light signal detector 12 or the starting signal START. The driving circuit 28 inputs the voltage VPP and drives the glare protecting plate 3. When the starting signal START or the light detecting signal PIN is not generated, the driving circuit 28 inputs the voltage VLCDR and drives the glare protecting plate 3.

The controller 18 determines whether the electromagnetic wave detecting signal RFIN applied from the electromagnetic wave detector 14 is higher than a predetermined value or not(Step 160). The controller 18 inputs the electromagnetic wave detecting signal RFIN and decides whether the welding can be continued or not. Accordingly, the electromagnetic wave of between 2 KHz and 400 KHz band as well as a light signal is generated according to the kind of a welding machine using arc, gas or etc. during the welding.

The controller 18 enables the driving control signal DOUT in the event that the electromagnetic wave detecting signal RFIN is higher than a predetermined value(step 180).

On the contrary, in the event that the electromagnetic wave detecting signal RFIN is not higher than a predetermined value, the controller 18 determines whether the light detecting signal PIN is generated or not(step 170).

In the event that the light detecting signal PIN is generated, the process proceeds to step 180. In the event that the light detecting signal PIN is not generated, the process proceeds to step 190.

In step 160 which determines whether the electromagnetic wave detecting signal RFIN is generated and in step 170 which determines whether the light detecting signal PIN is generated, the controller 18 determines that the welding is being performed and generates the driving control signal DOUT in the event that the electromagnetic wave detecting signal RFIN is higher than a predetermined value or the light detecting signal PIN is generated. Accordingly, the driving circuit 28 operates to keep the glare protecting plate 3 turned on.

After performing the step 180 or step 190, the controller 18 is shifted to a stop mode(step 200). The controller 18 repeatedly performs operations of the above-described steps.

As shown above, according to the present invention, a controller is shifted to an operating mode and operates on/off of the glare protecting plate only in the event that a light detecting signal is changed. In the event that a light is not changed, the controller maintains a stop mode so that the operating time of the controller becomes shorter. Accordingly, the power consumption is decreased by using the controller.

Also, when a light is applied to the device of the present invention, it detects a change of light and automatically operates the glare protecting plate even though a worker does not manipulate a switch manually.

Figure 4:
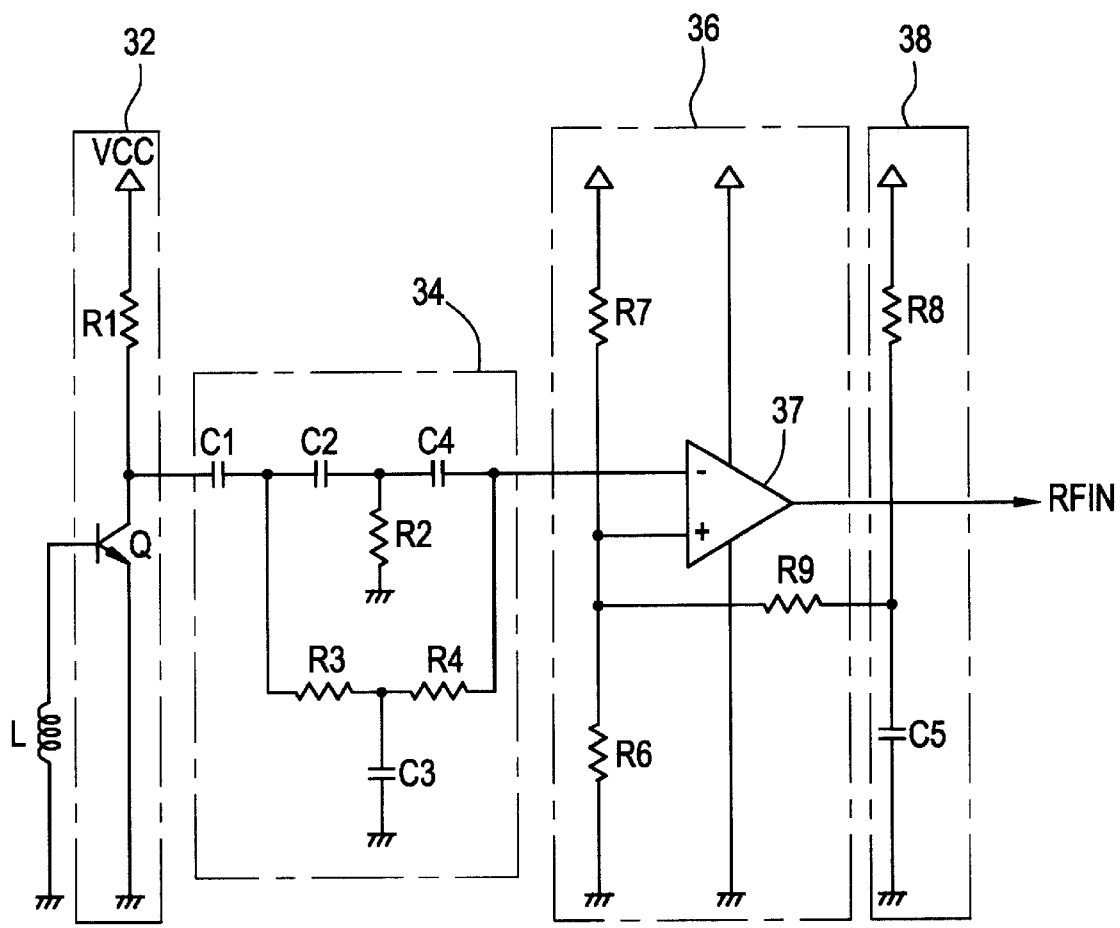
FIG. 4 is a circuit diagram illustrating an embodiment of the electromagnetic wave detector shown in FIG. 2.

FIG. 4 is a circuit diagram illustrating an embodiment of the electromagnetic wave detector 14 shown in FIG. 2 according to the present invention, comprising a resonator 32, a filter 34, a comparing circuit 36, and a time constant circuit 38.

Referring to FIG. 4, the antenna 7 shown in FIG. 2 is represented by a coil L.

A structure of circuits shown FIG. 4 is described in detail below.

Resonator 32 is composed of a resistor R1 and a NPN transistor Q connected in series between a power supply voltage VCC and a ground voltage.

The coil L is connected between a gate of the NPN transistor Q and a ground voltage.

Filter 34 comprises a capacitor C1, a resistor R3 and a capacitor C3 connected in series between a collector of the NPN transistor Q and a ground voltage; a capacitor C2 and a resistor R2 connected in series between a connection point of the capacitor C1 and the resistor R3, and a ground voltage; and a capacitor C4 and a resistor R4 connected in series between a common node of the capacitor C2 and the resistor R2, and a common node of the resistor R3 and the capacitor C3.

Comparing circuit 36 comprises resistors R6 and R7 connected in series between a power supply and a ground voltage; a comparator 37 having a negative input terminal connected to a common node of the capacitor C4 and the resistor R4, and a positive input terminal connected to a common node of the resistors R6 and R7; and a resistor R9 connected between the common node of the resistors R6 and R7, and an output terminal of the comparator 37.

Time constant circuit 38 comprises a resistor R8 connected between a power supply and the output terminal of the comparator 37, and a capacitor C5 connected between the output terminal of the comparator 37 and a ground voltage.

Operation of the electromagnetic wave detector is described below.

Coil L detects an electromagnetic wave signal from the surroundings.

In the resonator 32, a current is applied to a base of the transistor Q through the coil L when the coil L detects an electromagnetic wave. A signal applied to the base of the transistor Q is a signal of a pulse type, and the transistor Q is repeatedly turned on and off in response to the signal. Thereby, an effective signal of the electromagnetic wave is outputted to a collector of the transistor Q. Accordingly, the resonator 32 outputs just an effective signal because a frequency resonance is performed by the inductance of the coil L, and the capacitance and a resistor which the transistor Q has.

Filter 34 eliminates the noise of the effective signal of the electromagnetic wave outputted from the resonator 32 and outputs it.

Comparing circuit 36 compares signals outputted from the filter 34 with divided voltage by the resistor R6 and R7, and generates the electromagnetic detecting signal RFIN. The comparing circuit 36 has a hysteresis characteristic by the resistor R9 connected between the output terminal and the positive input terminal of the comparator 37.

Time constant circuit 38 is composed of an integrating circuit and smoothes the electromagnetic wave detecting signal RFIN.

Accordingly, the electromagnetic wave signal detector 14 of the present invention comprises the resonator, the filter, the comparing circuit, and the time constant circuit, and detects a frequency element of an effective band generated in the welding and the cutting torch to generate the electromagnetic wave detecting signal RFIN.

According to the present invention, the glare protecting device is shifted to a operating mode in the event that a light is changed, without any manual switch needed to be manipulated. In the event that a light is not changed, the device is automatically shifted to a stop mode, so that the operating time of the controller becomes short and the power consumption is decreased.

According to the present invention, the controller as a microcomputer controls on/off of the glare protecting plate in the glare protecting device, thereby the operating speed can be improved.

The glare protecting device and a method of controlling thereof control on/off of the glare protecting plate by detecting a light and/or an electromagnetic wave generated in the welding or the cutting torch. Thereby, a malfunction caused by a light or an electromagnetic wave of a noise element can be prevented.

While this invention has been particularly shown and described with reference to preferred embodiments thereof, it will be understood by those skilled in the art that various changes in form and details may be made therein without departing from the spirit and scope of the invention.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A glare protecting device comprising:
    a glare protecting plate of which optical transmittance is adjusted by a driving signal;
    a solar cell which generates a solar voltage when light is applied thereto;
    a voltage generator for being charged by said solar voltage and generating a reset voltage;
    an optical detector for generating a light detecting signal by detecting a change in said light;
    a non-optical detector for generating an electromagnetic wave detecting signal by detecting an electromagnetic wave;
    a controller shifting into an operating mode in response to said light detecting signal, for generating a starting control signal and a driving control signal for starting time and driving time, respectively, of said operating mode in response to said electromagnetic wave detecting signal and said light detecting signal; and
    a driving means for selectively generating a starting voltage in response to said starting control signal and a driving voltage in response to said driving control signal as said driving signal,
    said controller:
        being reset in response to said reset voltage from said voltage generator;
        generating said starting control signal in response to said light detecting signal when said driving control signal is disabled in said operating mode;
        enabling said driving control signal in response to said electromagnetic wave detecting signal or said light detecting signal after generating said starting control signal in said operating mode;
        shifting into and maintaining a stop mode until shifting into said operating mode.

2. The glare protecting device of claim 1, wherein said driving means comprises:
    an oscillator for generating an oscillating voltage by using said solar voltage;
    a power generator for generating said starting voltage and said driving voltage by amplifying said oscillating voltage;
    a starting circuit for outputting said starting voltage in response to said starting control signal;
    an intensity controller for outputting said driving voltage and adjusting the optical transmittance of said glare protecting plate by controlling said driving voltage; and
    a driving circuit for receiving said starting voltage and said driving voltage and providing said driving signal to said glare protecting plate in response to said driving control signal.

3. The glare protecting device of claim 1, wherein said non-optical detector comprises:
    an antenna for detecting an electromagnetic wave;
    a resonator in which an electromagnetic wave inputted through said antenna resonates;
    a filter for detecting a frequency signal of an effective band from output signals of said resonator;
    a comparator for comparing an output value of said filter with a predetermined value; and
    a time constant circuit for smoothing output signal of said comparator.

4. The glare protecting device of claim 3, wherein said antenna is a coil.

5. The glare protecting device of claim 1, wherein said glare protecting plate is a liquid crystal display.

6. The glare protecting device of claim 1, wherein said non-optical detector comprising:
    an electromagnetic wave detector for detecting an electromagnetic wave to generate said electromagnetic wave detecting signal; and
    a temperature detector for generating a temperature detecting signal by detecting the ambient temperature.

7. The glare protecting device of claim 6, wherein said driving means comprises:
   an oscillator for generating a signal oscillated by said solar voltage;
   a power generator for generating said starting voltage and said driving voltage by performing a boosting operation in response to a signal of said oscillator;
   a starting circuit for outputting said starting voltage in response to said starting signal;
   an intensity controller for controlling the transmittance of said glare protecting plate by controlling said driving voltage; and
   a driving circuit enabled by said driving control signal and for generating said driving signal by inputting said starting voltage and said driving voltage controlled by said intensity controller.

8. The glare protecting device of claim 6, wherein said non-optical detector comprises:
   an antenna for detecting an electromagnetic wave;
   a resonator in which said electromagnetic wave inputted through said antenna resonates;
   a filter for detecting a frequency signal of an efficient band from output signals of said resonator;
   a comparator for comparing an output value of said filter with a predetermined value; and
   a time constant circuit for smoothing output signal of said comparator.

9. The glare protecting device of claim 8, wherein said antenna is a coil.

10. The glare protecting device of claim 6, wherein said glare protecting plate is a liquid crystal display.

11. The glare protecting device of claim 6, wherein said controller generates said starting control signal in response to said light detecting signal or said temperature detecting signal.

12. The glare protecting device of claim 6, wherein said starting voltage has a voltage value higher than that of said driving voltage.

13. A method of controlling a glare protecting device comprising:
   a light detector for generating a light detecting signal by detecting a change in light applied to said glare protecting device;
   an electromagnetic wave detector for generating an electromagnetic wave detecting signal by detecting an electromagnetic wave; and
   a controller for controlling optical transmittance of a glare protecting plate in response to said light detecting signal and said electromagnetic wave detecting signal,
   wherein said method comprises:
      shifting into an operating mode in response to said light detecting signal;
      providing said glare protecting plate with a first driving signal and a second driving signal in starting time and driving time, respectively, of said operating mode as a driving signal to adjust optical transmittance of said glare protecting plate, wherein said optical transmittance of said glare protecting plate decreases more rapidly in said starting time than in said driving time; and
      shifting said glare protecting plate into a stop mode after said operating mode until said light detector detects a change in said light.

14. The method of controlling the glare protecting device of claim 13, wherein said first driving signal has a voltage value higher than that of said second driving signal.

15. The method of claim 13, wherein said glare protecting device further comprises a temperature detector for generating a temperature detecting signal by detecting the ambient temperature, said method further comprising controlling said starting time of said operating mode in response to said temperature detecting signal or said light detecting signal.

16. The method of controlling the glare protecting device of claim 15, wherein said glare protecting plate is a liquid crystal display.

* * * * *